(12) United States Patent  (10) Patent No.: US 9,125,979 B2
Behzadi et al.  (45) Date of Patent: Sep. 8, 2015

(54) FLUID TRANSFER PORT INFORMATION SYSTEM

(75) Inventors: Yashar Behzadi, San Francisco, CA (US); Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 1166 days.

(21) Appl. No.: 12/258,298

(22) Filed: Oct. 24, 2008

(65) Prior Publication Data

US 2009/0112178 A1  Apr. 30, 2009

Related U.S. Application Data

(60) Provisional application No. 60/982,661, filed on Oct. 25, 2007.

(51) Int. Cl.
*A61M 5/14* (2006.01)
*A61M 5/142* (2006.01)
(Continued)

(52) U.S. Cl.
CPC ............... *A61M 5/14* (2013.01); *A61M 5/142* (2013.01); *G06F 19/3462* (2013.01); *G06F 19/3468* (2013.01); *A61M 39/0247* (2013.01); *A61M 2205/276* (2013.01);
(Continued)

(58) Field of Classification Search
CPC ............... A61M 2205/276; A61M 2205/3538; A61M 2205/52; A61M 2205/6027; A61M 2205/6054; A61M 39/0247; A61M 5/14; A61M 5/142; G06F 19/3462; G06F 19/3468
USPC ............ 604/65–73, 500, 503, 501, 220; 600/301, 300, 547
See application file for complete search history.

(56) References Cited

U.S. PATENT DOCUMENTS 3,812,854 A  5/1974  Michaels et al.
3,880,146 A  4/1975  Everett et al.
(Continued)

FOREIGN PATENT DOCUMENTS

JP  6296633  10/1994
JP  2001-061799  3/2001
(Continued)

OTHER PUBLICATIONS

Nikander et al., "The Adaptive Delivery System in a Telehealth Setting: Patient Acceptance, Performance and Feasibility" Journal of Aerosol Medicine and Pulmonary Drug Delivery; vol. 23, Supp. 1, (2010) pp. S21-S27.
(Continued)

*Primary Examiner* — Imani Hayman
(74) *Attorney, Agent, or Firm* — K&L Gates LLP (57) ABSTRACT

Methods are provided for associating a specific one of two or more distinct fluid transfer ports of a patient with a given fluid transfer event of fluid from a parenteral fluid delivery device. Aspects of the methods include establishing a fluid transfer connection between the parenteral fluid delivery device and the patient via one of the two or more distinct fluid transfer ports and transmitting a fluid transfer signal between the parenteral fluid delivery device and a patient associated identifier using the patient's body as a signal conduction medium. Association may result in identification of the fluid transfer port that will be, is being or has been employed for the given fluid transfer event. Also provided are systems for practicing methods of the invention.

18 Claims, 2 Drawing Sheets

(51) Int. Cl.
*G06F 19/00* (2011.01)
*A61M 39/02* (2006.01)

(52) U.S. Cl.
CPC ... *A61M 2205/3538* (2013.01); *A61M 2205/52* (2013.01); *A61M 2205/6027* (2013.01); *A61M 2205/6054* (2013.01)

(56) References Cited

U.S. PATENT DOCUMENTS

| | | | |
|---|---|---|---|
| 4,403,989 A | 9/1983 | Christensen et al. |
| 4,475,905 A | 10/1984 | Himmelstrup |
| 4,487,602 A | 12/1984 | Christensen et al. |
| 4,529,401 A | 7/1985 | Leslie et al. |
| 4,551,133 A | 11/1985 | Zegers de Beyl et al. |
| 4,621,644 A | 11/1986 | Ellers |
| 4,669,479 A | 6/1987 | Dunseath, Jr. |
| 4,705,503 A | 11/1987 | Dorman et al. |
| 4,795,429 A | 1/1989 | Feldstein |
| 4,850,967 A | 7/1989 | Cosmai |
| 4,911,916 A | 3/1990 | Cleary |
| 4,922,901 A | 5/1990 | Brooks et al. |
| 5,006,342 A | 4/1991 | Cleary et al. |
| 5,125,888 A | 6/1992 | Howard et al. |
| 5,135,479 A | 8/1992 | Sibalis et al. |
| 5,156,911 A | 10/1992 | Stewart |
| 5,167,649 A | 12/1992 | Zook |
| 5,190,522 A | 3/1993 | Wojcicki et al. |
| 5,205,292 A | 4/1993 | Czar et al. |
| 5,213,568 A | 5/1993 | Lattin et al. |
| 5,246,418 A | 9/1993 | Haynes et al. |
| 5,284,133 A | 2/1994 | Burns et al. |
| 5,300,299 A | 4/1994 | Sweet et al. |
| 5,317,506 A | 5/1994 | Coutre et al. |
| 5,331,953 A | 7/1994 | Andersson et al. |
| 5,351,695 A | 10/1994 | Mills et al. |
| 5,363,842 A | 11/1994 | Mishelevich et al. |
| 5,364,838 A | 11/1994 | Rubsamen |
| 5,394,866 A | 3/1995 | Ritson et al. |
| 5,404,871 A | 4/1995 | Goodman et al. |
| 5,415,866 A | 5/1995 | Zook |
| 5,423,750 A | 6/1995 | Spiller |
| 5,479,920 A | 1/1996 | Piper et al. |
| 5,487,378 A | 1/1996 | Robertson et al. |
| 5,505,195 A | 4/1996 | Wolf |
| 5,505,958 A | 4/1996 | Bello et al. |
| 5,507,277 A | 4/1996 | Rubsamen et al. |
| 5,509,404 A | 4/1996 | Lloyd et al. |
| 5,522,378 A | 6/1996 | Ritson et al. |
| 5,527,288 A | 6/1996 | Gross et al. |
| 5,536,503 A | 7/1996 | Kitchell et al. |
| 5,540,669 A | 7/1996 | Sage et al. |
| 5,542,410 A | 8/1996 | Goodman et al. |
| 5,556,421 A | 9/1996 | Prutchi et al. |
| 5,570,682 A | 11/1996 | Johnson |
| 5,586,550 A | 12/1996 | Ivri et al. |
| 5,587,237 A | 12/1996 | Korpman |
| 5,593,390 A | 1/1997 | Castellano et al. |
| RE35,474 E | 3/1997 | Woodard et al. |
| 5,608,647 A | 3/1997 | Rubsamen et al. |
| 5,616,124 A | 4/1997 | Hague et al. |
| 5,622,162 A | 4/1997 | Johannson et al. |
| 5,622,180 A | 4/1997 | Tammi et al. |
| 5,634,899 A | 6/1997 | Shapland et al. |
| 5,645,855 A | 7/1997 | Lorenz |
| 5,655,516 A | 8/1997 | Goodman et al. |
| 5,655,523 A | 8/1997 | Hodson et al. |
| 5,656,286 A | 8/1997 | Miranda et al. |
| 5,666,945 A | 9/1997 | Davenport |
| 5,676,129 A | 10/1997 | Rocci, Jr. et al. |
| 5,686,099 A | 11/1997 | Sablotsky et al. |
| 5,688,232 A | 11/1997 | Flower |
| 5,694,919 A | 12/1997 | Rubsamen et al. |
| 5,694,920 A | 12/1997 | Abrams et al. |
| 5,697,899 A | 12/1997 | Hillman et al. |
| 5,709,202 A | 1/1998 | Lloyd et al. |
| 5,713,349 A | 2/1998 | Keaney |
| 5,724,986 A | 3/1998 | Jones, Jr. et al. |
| 5,740,793 A | 4/1998 | Hodson et al. |
| 5,746,711 A | 5/1998 | Sibalis et al. |
| 5,781,442 A | 7/1998 | Engleson et al. |
| 5,794,612 A | 8/1998 | Wachter et al. |
| 5,807,375 A | 9/1998 | Gross et al. |
| 5,809,997 A | 9/1998 | Wolf |
| 5,810,888 A | 9/1998 | Fenn |
| 5,813,397 A | 9/1998 | Goodman et al. |
| 5,823,179 A | 10/1998 | Grychowski et al. |
| 5,826,570 A | 10/1998 | Goodman et al. |
| 5,830,175 A | 11/1998 | Flower |
| 5,839,430 A | 11/1998 | Cama |
| 5,843,014 A | 12/1998 | Lattin et al. |
| 5,848,991 A | 12/1998 | Gross et al. |
| 5,851,197 A | 12/1998 | Marano et al. |
| 5,857,994 A | 1/1999 | Flower |
| 5,860,957 A | 1/1999 | Jacobsen et al. |
| 5,865,786 A | 2/1999 | Sibalis et al. |
| 5,865,787 A | 2/1999 | Shapland et al. |
| 5,873,835 A | 2/1999 | Hastings et al. |
| 5,894,841 A | 4/1999 | Voges |
| 5,906,579 A | 5/1999 | Vander et al. |
| 5,906,597 A | 5/1999 | McPhee et al. |
| 5,921,237 A | 7/1999 | Eisele et al. |
| 5,924,997 A | 7/1999 | Campbell |
| 5,925,021 A | 7/1999 | Castellano et al. |
| 5,928,201 A | 7/1999 | Poulsen et al. |
| 5,960,792 A | 10/1999 | Lloyd et al. |
| 5,967,986 A | 10/1999 | Cimochowski et al. |
| 5,967,989 A | 10/1999 | Cimochowski et al. |
| 5,991,655 A | 11/1999 | Gross et al. |
| 5,997,501 A | 12/1999 | Gross et al. |
| 6,006,747 A | 12/1999 | Eisele et al. |
| 6,012,454 A | 1/2000 | Hodson et al. |
| 6,018,680 A | 1/2000 | Flower |
| 6,024,976 A | 2/2000 | Miranda et al. |
| 6,029,083 A | 2/2000 | Flower et al. |
| 6,053,873 A | 4/2000 | Govari et al. |
| 6,053,888 A | 4/2000 | Kong |
| 6,055,980 A | 5/2000 | Mecikalski et al. |
| RE36,754 E | 6/2000 | Noel |
| 6,076,519 A | 6/2000 | Johnson |
| 6,085,740 A | 7/2000 | Ivri et al. |
| 6,085,742 A | 7/2000 | Wachter |
| 6,095,141 A | 8/2000 | Armer et al. |
| 6,105,571 A | 8/2000 | Coffee |
| 6,109,260 A | 8/2000 | Bathe |
| 6,116,233 A | 9/2000 | Denyer et al. |
| 6,119,684 A | 9/2000 | Nohl et al. |
| 6,125,844 A | 10/2000 | Samiotes |
| 6,142,146 A | 11/2000 | Abrams et al. |
| 6,148,815 A | 11/2000 | Wolf |
| 6,152,130 A | 11/2000 | Abrams et al. |
| 6,196,218 B1 | 3/2001 | Voges |
| 6,196,219 B1 | 3/2001 | Hess et al. |
| 6,198,966 B1 | 3/2001 | Heruth |
| 6,202,642 B1 | 3/2001 | Mckinnon et al. |
| 6,221,383 B1 | 4/2001 | Miranda et al. |
| 6,231,560 B1 | 5/2001 | Bui et al. |
| 6,237,398 B1 | 5/2001 | Porat et al. |
| 6,237,589 B1 | 5/2001 | Denyer et al. |
| 6,237,594 B1 | 5/2001 | Davenport |
| 6,245,026 B1 | 6/2001 | Campbell et al. |
| 6,251,079 B1 | 6/2001 | Gambale et al. |
| 6,254,573 B1 | 7/2001 | Haim et al. |
| 6,256,533 B1 | 7/2001 | Yuzhakov et al. |
| 6,260,549 B1 | 7/2001 | Sosiak |
| 6,269,340 B1 | 7/2001 | Ford et al. |
| 6,272,370 B1 | 8/2001 | Gillies et al. |
| 6,283,951 B1 | 9/2001 | Flaherty et al. |
| 6,283,953 B1 | 9/2001 | Ayer et al. |
| 6,309,370 B1 | 10/2001 | Haim et al. |
| 6,315,719 B1 | 11/2001 | Rose et al. |
| 6,316,022 B1 | 11/2001 | Mantelle |
| 6,318,361 B1 | 11/2001 | Sosiak |
| 6,327,486 B1 | 12/2001 | Nissila et al. |

(56) References Cited

U.S. PATENT DOCUMENTS

| | | |
|---|---|---|
| 6,340,357 B1 | 1/2002 | Poulsen et al. |
| 6,349,724 B1 | 2/2002 | Burton et al. |
| 6,352,715 B1 | 3/2002 | Hwang et al. |
| 6,377,848 B1 | 4/2002 | Garde et al. |
| 6,378,520 B1 | 4/2002 | Davenport |
| 6,385,488 B1 | 5/2002 | Flower et al. |
| 6,390,088 B1 | 5/2002 | Nohl et al. |
| 6,394,997 B1 | 5/2002 | Lemelson |
| 6,397,838 B1 | 6/2002 | Zimlich et al. |
| 6,406,426 B1 | 6/2002 | Reuss et al. |
| 6,413,238 B1 | 7/2002 | Maget |
| 6,422,236 B1 | 7/2002 | Nilsson et al. |
| 6,425,392 B1 | 7/2002 | Sosiak |
| 6,427,684 B2 | 8/2002 | Ritsche et al. |
| 6,431,171 B1 | 8/2002 | Burton |
| 6,435,175 B1 | 8/2002 | Stenzler |
| 6,443,146 B1 | 9/2002 | Voges |
| 6,448,303 B1 | 9/2002 | Paul |
| 6,453,195 B1 | 9/2002 | Thompson |
| 6,468,242 B1 | 10/2002 | Wilson et al. |
| 6,484,721 B1 | 11/2002 | Bliss |
| 6,485,461 B1 | 11/2002 | Mason et al. |
| 6,516,796 B1 | 2/2003 | Cox et al. |
| 6,517,481 B2 | 2/2003 | Hoek et al. |
| 6,517,527 B2 | 2/2003 | Gambale et al. |
| 6,520,928 B1 | 2/2003 | Junior et al. |
| 6,527,759 B1 | 3/2003 | Tachibana et al. |
| 6,533,733 B1 | 3/2003 | Ericson et al. |
| 6,536,423 B2 | 3/2003 | Conway |
| 6,540,154 B1 | 4/2003 | Ivri et al. |
| 6,564,093 B1 | 5/2003 | Ostrow et al. |
| 6,568,390 B2 | 5/2003 | Nichols et al. |
| 6,575,932 B1 | 6/2003 | O'Brien et al. |
| 6,578,741 B2 | 6/2003 | Ritsche et al. |
| 6,582,393 B2 | 6/2003 | Sage |
| 6,584,971 B1 | 7/2003 | Denyer et al. |
| 6,585,698 B1 | 7/2003 | Packman et al. |
| 6,589,229 B1 | 7/2003 | Connelly et al. |
| 6,599,281 B1 | 7/2003 | Struys et al. |
| 6,605,072 B2 | 8/2003 | Struys et al. |
| 6,606,989 B1 | 8/2003 | Brand et al. |
| 6,607,508 B2 | 8/2003 | Knauer |
| 6,615,827 B2 | 9/2003 | Greenwood et al. |
| 6,629,524 B1 | 10/2003 | Goodall et al. |
| 6,640,804 B2 | 11/2003 | Ivri et al. |
| 6,651,651 B1 | 11/2003 | Bonney et al. |
| 6,655,381 B2 | 12/2003 | Keane et al. |
| 6,656,148 B2 | 12/2003 | Das et al. |
| 6,678,555 B2 | 1/2004 | Flower et al. |
| 6,685,648 B2 | 2/2004 | Flaherty et al. |
| 6,705,316 B2 | 3/2004 | Blythe et al. |
| 6,715,487 B2 | 4/2004 | Nichols et al. |
| 6,723,077 B2 | 4/2004 | Pickup et al. |
| 6,726,661 B2 | 4/2004 | Munk et al. |
| 6,728,574 B2 | 4/2004 | Ujhelyi et al. |
| 6,745,761 B2 | 6/2004 | Christup et al. |
| 6,745,764 B2 | 6/2004 | Hickle |
| 6,746,429 B2 | 6/2004 | Sadowski et al. |
| 6,748,945 B2 | 6/2004 | Grychowski et al. |
| 6,796,305 B1 | 9/2004 | Banner et al. |
| 6,796,956 B2 | 9/2004 | Hartlaub et al. |
| 6,807,965 B1 | 10/2004 | Hickle |
| 6,810,290 B2 | 10/2004 | Lebel et al. |
| 6,854,461 B2 | 2/2005 | Nichols et al. |
| 6,858,011 B2 | 2/2005 | Sehgal |
| 6,866,037 B1 | 3/2005 | Aslin et al. |
| 6,886,557 B2 | 5/2005 | Childers et al. |
| 6,893,415 B2 | 5/2005 | Madsen et al. |
| 6,902,740 B2 | 6/2005 | Schaberg et al. |
| 6,923,784 B2 | 8/2005 | Stein et al. |
| 6,941,168 B2 | 9/2005 | Girouard |
| 6,949,081 B1 | 9/2005 | Chance |
| 6,958,691 B1 | 10/2005 | Anderson et al. |
| 6,961,601 B2 | 11/2005 | Matthews et al. |
| 6,971,383 B2 | 12/2005 | Hickey et al. |
| 6,981,499 B2 | 1/2006 | Anderson et al. |
| 6,983,652 B2 | 1/2006 | Blakely et al. |
| 6,985,771 B2 | 1/2006 | Fischell et al. |
| 6,985,870 B2 | 1/2006 | Martucci et al. |
| 6,990,975 B1 | 1/2006 | Jones et al. |
| 6,999,854 B2 | 2/2006 | Roth |
| 7,010,337 B2 | 3/2006 | Furnary et al. |
| 7,034,692 B2 | 4/2006 | Hickle |
| 7,040,314 B2 | 5/2006 | Nguyen et al. |
| 7,044,911 B2 | 5/2006 | Drinan et al. |
| 7,047,964 B2 | 5/2006 | Bacon |
| 7,054,782 B2 | 5/2006 | Hartlaub |
| 7,072,802 B2 | 7/2006 | Hartlaub |
| 7,089,935 B1 | 8/2006 | Rand |
| 7,097,853 B1 | 8/2006 | Garbe et al. |
| 7,104,972 B2 | 9/2006 | Moller et al. |
| 7,107,988 B2 | 9/2006 | Pinon et al. |
| 7,108,680 B2 | 9/2006 | Rohr et al. |
| 7,117,867 B2 | 10/2006 | Cox et al. |
| 7,138,088 B2 | 11/2006 | Wariar et al. |
| 7,147,170 B2 | 12/2006 | Nguyen et al. |
| 7,168,597 B1 | 1/2007 | Jones et al. |
| 7,181,261 B2 | 2/2007 | Silver et al. |
| 7,191,777 B2 | 3/2007 | Brand et al. |
| 7,198,172 B2 | 4/2007 | Harvey et al. |
| 7,201,734 B2 | 4/2007 | Hickle |
| 7,204,823 B2 | 4/2007 | Estes et al. |
| 7,220,240 B2 | 5/2007 | Struys et al. |
| 7,225,805 B2 | 6/2007 | Bacon |
| 7,232,435 B2 | 6/2007 | Hildebrand et al. |
| 7,242,981 B2 | 7/2007 | Ginggen |
| 7,247,154 B2 | 7/2007 | Hickle |
| 7,261,733 B1 | 8/2007 | Brown et al. |
| 7,267,121 B2 | 9/2007 | Ivri et al. |
| 7,278,983 B2 | 10/2007 | Ireland et al. |
| 7,291,126 B2 | 11/2007 | Shekalim |
| 7,320,675 B2 | 1/2008 | Pastore et al. |
| 7,322,352 B2 | 1/2008 | Minshull et al. |
| 7,322,355 B2 | 1/2008 | Jones et al. |
| 7,331,340 B2 | 2/2008 | Barney |
| 7,342,660 B2 | 3/2008 | Altobelli et al. |
| 7,347,200 B2 | 3/2008 | Jones et al. |
| 7,347,202 B2 | 3/2008 | Aslin et al. |
| 7,347,851 B1 | 3/2008 | Kriksunov |
| 7,367,968 B2 | 5/2008 | Rosenberg et al. |
| 7,380,550 B2 | 6/2008 | Sexton et al. |
| 7,382,263 B2 | 6/2008 | Danowski et al. |
| 7,383,837 B2 | 6/2008 | Robertson et al. |
| 7,387,121 B2 | 6/2008 | Harvey |
| 7,390,311 B2 | 6/2008 | Hildebrand et al. |
| 7,397,730 B2 | 7/2008 | Skyggebjerg et al. |
| 7,415,384 B2 | 8/2008 | Hartlaub |
| 7,424,888 B2 | 9/2008 | Harvey et al. |
| 7,455,667 B2 | 11/2008 | Uhland et al. |
| 7,458,373 B2 | 12/2008 | Nichols et al. |
| 7,467,629 B2 | 12/2008 | Rand |
| 7,483,743 B2 | 1/2009 | Mann et al. |
| 7,488,305 B2 | 2/2009 | Mickley et al. |
| 7,495,546 B2 | 2/2009 | Lintell et al. |
| 7,510,551 B2 | 3/2009 | Uhland et al. |
| 7,517,332 B2 | 4/2009 | Tonelli et al. |
| 7,520,278 B2 | 4/2009 | Crowder et al. |
| 7,530,352 B2 | 5/2009 | Childers et al. |
| 7,530,975 B2 | 5/2009 | Hunter |
| 7,537,590 B2 | 5/2009 | Santini et al. |
| 7,542,798 B2 | 6/2009 | Girouard |
| 7,544,190 B2 | 6/2009 | Pickup et al. |
| 7,548,314 B2 | 6/2009 | Altobelli et al. |
| 7,549,421 B2 | 6/2009 | Levi et al. |
| 7,552,728 B2 | 6/2009 | Bonney et al. |
| 7,554,090 B2 | 6/2009 | Coleman et al. |
| 7,575,003 B2 | 8/2009 | Rasmussen et al. |
| 7,581,540 B2 | 9/2009 | Hale et al. |
| 7,597,099 B2 | 10/2009 | Jones et al. |
| 7,631,643 B2 | 12/2009 | Morrison et al. |
| 7,670,329 B2 | 3/2010 | Flaherty et al. |
| 7,672,726 B2 | 3/2010 | Ginggen |
| 7,677,467 B2 | 3/2010 | Fink et al. |
| 7,686,788 B2 | 3/2010 | Freyman et al. |

(56) References Cited

U.S. PATENT DOCUMENTS

| | | |
|---|---|---|
| 7,699,060 B2 | 4/2010 | Bahm |
| 7,699,829 B2 | 4/2010 | Harris et al. |
| 7,708,011 B2 | 5/2010 | Hochrainer et al. |
| 7,713,229 B2 | 5/2010 | Veit et al. |
| 7,715,919 B2 | 5/2010 | Osorio et al. |
| 7,717,877 B2 | 5/2010 | Lavi et al. |
| 7,725,161 B2 | 5/2010 | Karmarker et al. |
| 7,783,344 B2 | 8/2010 | Lackey et al. |
| 7,904,133 B2 | 3/2011 | Gehman et al. |
| 8,016,798 B2 | 9/2011 | Sparks et al. |
| 8,162,899 B2 | 4/2012 | Tennican |
| 8,777,894 B2 * | 7/2014 | Butterfield et al. ............. 604/65 |
| 2001/0000802 A1 | 5/2001 | Soykan et al. |
| 2001/0022279 A1 | 9/2001 | Denyer et al. |
| 2002/0000225 A1 | 1/2002 | Schuler et al. |
| 2002/0002349 A1 | 1/2002 | Flaherty et al. |
| 2002/0010432 A1 | 1/2002 | Klitmose et al. |
| 2002/0013615 A1 | 1/2002 | Haim et al. |
| 2002/0026940 A1 | 3/2002 | Brooker et al. |
| 2002/0077852 A1 | 6/2002 | Ford et al. |
| 2002/0099328 A1 | 7/2002 | Scheiner et al. |
| 2002/0120236 A1 | 8/2002 | Diaz et al. |
| 2002/0153006 A1 | 10/2002 | Zimlich et al. |
| 2002/0189612 A1 | 12/2002 | Rand et al. |
| 2002/0189615 A1 | 12/2002 | Henry et al. |
| 2002/0198493 A1 | 12/2002 | Diaz et al. |
| 2003/0004236 A1 | 1/2003 | Meade et al. |
| 2003/0078561 A1 | 4/2003 | Gambale et al. |
| 2003/0079744 A1 | 5/2003 | Bonney et al. |
| 2003/0094508 A1 | 5/2003 | Peng et al. |
| 2003/0136418 A1 | 7/2003 | Behm et al. |
| 2003/0140921 A1 | 7/2003 | Smith et al. |
| 2003/0150446 A1 | 8/2003 | Patel et al. |
| 2003/0159693 A1 | 8/2003 | Melker et al. |
| 2003/0168057 A1 | 9/2003 | Snyder et al. |
| 2003/0171738 A1 | 9/2003 | Konieczynski et al. |
| 2003/0176804 A1 | 9/2003 | Melker |
| 2003/0183226 A1 | 10/2003 | Brand et al. |
| 2003/0205229 A1 | 11/2003 | Crockford et al. |
| 2004/0004133 A1 | 1/2004 | Ivri et al. |
| 2004/0019321 A1 | 1/2004 | Sage et al. |
| 2004/0025871 A1 | 2/2004 | Davies et al. |
| 2004/0031331 A1 | 2/2004 | Blakley et al. |
| 2004/0050385 A1 | 3/2004 | Bonney et al. |
| 2004/0089299 A1 | 5/2004 | Bonney et al. |
| 2004/0098117 A1 | 5/2004 | Hossainy et al. |
| 2004/0106902 A1 | 6/2004 | Diaz et al. |
| 2004/0122530 A1 | 6/2004 | Hansen et al. |
| 2004/0133154 A1 | 7/2004 | Flaherty et al. |
| 2004/0139963 A1 | 7/2004 | Ivri et al. |
| 2004/0158167 A1 | 8/2004 | Smith et al. |
| 2004/0181196 A1 | 9/2004 | Pickup et al. |
| 2004/0187864 A1 | 9/2004 | Adams et al. |
| 2004/0193453 A1 | 9/2004 | Butterfield et al. |
| 2004/0210199 A1 | 10/2004 | Atterbury et al. |
| 2004/0254435 A1 | 12/2004 | Mathews et al. |
| 2005/0010166 A1 | 1/2005 | Hickle |
| 2005/0045734 A1 | 3/2005 | Peng et al. |
| 2005/0059924 A1 | 3/2005 | Katz et al. |
| 2005/0072421 A1 | 4/2005 | Suman et al. |
| 2005/0081845 A1 | 4/2005 | Barney et al. |
| 2005/0087189 A1 | 4/2005 | Crockford et al. |
| 2005/0137626 A1 | 6/2005 | Pastore et al. |
| 2005/0139651 A1 | 6/2005 | Lim et al. |
| 2005/0155602 A1 | 7/2005 | Lipp |
| 2005/0165342 A1 | 7/2005 | Odland |
| 2005/0172956 A1 | 8/2005 | Childers et al. |
| 2005/0172958 A1 | 8/2005 | Singer et al. |
| 2005/0183725 A1 | 8/2005 | Gumaste et al. |
| 2005/0203637 A1 | 9/2005 | Edman et al. |
| 2005/0235732 A1 | 10/2005 | Rush |
| 2005/0236501 A1 | 10/2005 | Zimlich et al. |
| 2005/0245906 A1 | 11/2005 | Makower et al. |
| 2005/0247312 A1 | 11/2005 | Davies et al. |
| 2005/0251289 A1 | 11/2005 | Bonney et al. |
| 2005/0274378 A1 | 12/2005 | Bonney et al. |
| 2006/0005842 A1 | 1/2006 | Rashad et al. |
| 2006/0030813 A1 | 2/2006 | Chance |
| 2006/0031099 A1 | 2/2006 | Vitello et al. |
| 2006/0037612 A1 | 2/2006 | Herder et al. |
| 2006/0042632 A1 | 3/2006 | Bishop et al. |
| 2006/0058593 A1 | 3/2006 | Drinan et al. |
| 2006/0090752 A1 | 5/2006 | Imondi et al. |
| 2006/0130832 A1 | 6/2006 | Schechter et al. |
| 2006/0131350 A1 | 6/2006 | Schechter et al. |
| 2006/0167530 A1 | 7/2006 | Flaherty et al. |
| 2006/0178586 A1 | 8/2006 | Dobak |
| 2006/0184087 A1 | 8/2006 | Wariar et al. |
| 2006/0191534 A1 | 8/2006 | Hickey et al. |
| 2006/0201499 A1 | 9/2006 | Muellinger et al. |
| 2006/0204532 A1 | 9/2006 | John et al. |
| 2006/0231093 A1 | 10/2006 | Burge et al. |
| 2006/0243277 A1 | 11/2006 | Denyer et al. |
| 2006/0253005 A1 | 11/2006 | Drinan |
| 2006/0283465 A1 | 12/2006 | Nickel |
| 2007/0023034 A1 | 2/2007 | Jongejan et al. |
| 2007/0023036 A1 | 2/2007 | Grychowski et al. |
| 2007/0043591 A1 | 2/2007 | Meretei et al. |
| 2007/0044793 A1 | 3/2007 | Kleinstreuer et al. |
| 2007/0060800 A1 | 3/2007 | Drinan et al. |
| 2007/0074722 A1 | 4/2007 | Giroux et al. |
| 2007/0088334 A1 | 4/2007 | Hillis et al. |
| 2007/0091273 A1 | 4/2007 | Sullivan et al. |
| 2007/0107517 A1 | 5/2007 | Arnold et al. |
| 2007/0123829 A1 | 5/2007 | Atterbury et al. |
| 2007/0125370 A1 | 6/2007 | Denyer et al. |
| 2007/0157931 A1 | 7/2007 | Parker et al. |
| 2007/0161879 A1 | 7/2007 | Say et al. |
| 2007/0169778 A1 | 7/2007 | Smith et al. |
| 2007/0197954 A1 | 8/2007 | Keenan |
| 2007/0203411 A1 | 8/2007 | Say et al. |
| 2007/0208322 A1 | 9/2007 | Rantala et al. |
| 2007/0209659 A1 | 9/2007 | Ivri et al. |
| 2007/0213658 A1 | 9/2007 | Hickle |
| 2007/0221218 A1 | 9/2007 | Warden et al. |
| 2007/0224128 A1 | 9/2007 | Dennis et al. |
| 2007/0240712 A1 | 10/2007 | Fleming et al. |
| 2007/0256688 A1 | 11/2007 | Schuster et al. |
| 2007/0258894 A1 | 11/2007 | Melker et al. |
| 2007/0295329 A1 | 12/2007 | Lieberman et al. |
| 2007/0299550 A1 | 12/2007 | Nishijima et al. |
| 2008/0009800 A1 | 1/2008 | Nickel |
| 2008/0021379 A1 | 1/2008 | Hickle |
| 2008/0039700 A1 | 2/2008 | Drinan et al. |
| 2008/0051667 A1 | 2/2008 | Goldreich |
| 2008/0058703 A1 | 3/2008 | Subramony et al. |
| 2008/0077080 A1 | 3/2008 | Hengstenberg et al. |
| 2008/0078382 A1 | 4/2008 | LeMahieu et al. |
| 2008/0078385 A1 | 4/2008 | Xiao et al. |
| 2008/0082001 A1 | 4/2008 | Hatlestad et al. |
| 2008/0086112 A1 | 4/2008 | Lo et al. |
| 2008/0091138 A1 | 4/2008 | Pastore et al. |
| 2008/0114299 A1 | 5/2008 | Damgaard-Sorensen et al. |
| 2008/0125759 A1 | 5/2008 | Konieczynski et al. |
| 2008/0142002 A1 | 6/2008 | Fink et al. |
| 2008/0147004 A1 | 6/2008 | Mann et al. |
| 2008/0147050 A1 | 6/2008 | Mann et al. |
| 2008/0173301 A1 | 7/2008 | Deaton et al. |
| 2008/0177246 A1 | 7/2008 | Sullican et al. |
| 2008/0178872 A1 | 7/2008 | Genova et al. |
| 2008/0200804 A1 | 8/2008 | Hartlep et al. |
| 2008/0216834 A1 | 9/2008 | Easley et al. |
| 2008/0221408 A1 | 9/2008 | Hoarau et al. |
| 2008/0262469 A1 | 10/2008 | Brister et al. |
| 2008/0269689 A1 | 10/2008 | Edwards et al. |
| 2008/0281276 A1 | 11/2008 | Shekalim |
| 2008/0306436 A1 | 12/2008 | Edwards et al. |
| 2008/0306444 A1 | 12/2008 | Brister et al. |
| 2008/0306449 A1 | 12/2008 | Kristensen et al. |
| 2009/0005763 A1 | 1/2009 | Makower et al. |
| 2009/0024112 A1 | 1/2009 | Edwards et al. |
| 2009/0025714 A1 | 1/2009 | Denyer et al. |
| 2009/0025718 A1 | 1/2009 | Denyer et al. |
| 2009/0048526 A1 | 2/2009 | Aarts et al. |

(56) References Cited

U.S. PATENT DOCUMENTS

| | | |
|---|---|---|
| 2009/0048556 A1 | 2/2009 | Durand |
| 2009/0056708 A1 | 3/2009 | Stenzler |
| 2009/0064997 A1 | 3/2009 | Li |
| 2009/0082829 A1 | 3/2009 | Panken et al. |
| 2009/0107503 A1 | 4/2009 | Baran |
| 2009/0151718 A1 | 6/2009 | Hunter et al. |
| 2009/0156952 A1 | 6/2009 | Hunter et al. |
| 2009/0163781 A1 | 6/2009 | Say et al. |
| 2009/0187167 A1 | 7/2009 | Sexton et al. |
| 2009/0194104 A1 | 8/2009 | Van Sickle |
| 2009/0211576 A1 | 8/2009 | Lehtonen et al. |
| 2009/0213373 A1 | 8/2009 | Altobelli et al. |
| 2009/0216194 A1 | 8/2009 | Elgard et al. |
| 2009/0221087 A1 | 9/2009 | Martin et al. |
| 2009/0227941 A1 | 9/2009 | Say et al. |
| 2009/0229607 A1 | 9/2009 | Brunnberg et al. |
| 2009/0241951 A1 | 10/2009 | Jafari et al. |
| 2009/0241955 A1 | 10/2009 | Jafari et al. |
| 2009/0270752 A1 | 10/2009 | Coifman |
| 2009/0301472 A1 | 12/2009 | Kim et al. |
| 2009/0314372 A1 | 12/2009 | Ruskewicz et al. |
| 2009/0326509 A1 | 12/2009 | Muse et al. |
| 2009/0326510 A1 | 12/2009 | Haefner et al. |
| 2010/0012120 A1 | 1/2010 | Herder et al. |
| 2010/0031957 A1 | 2/2010 | McIntosh |
| 2010/0049004 A1 | 2/2010 | Edman et al. |
| 2010/0049172 A1 | 2/2010 | Chance |
| 2010/0078015 A1 | 4/2010 | Imran |
| 2010/0094099 A1 | 4/2010 | Levy et al. |
| 2010/0099967 A1 | 4/2010 | Say et al. |
| 2010/0100078 A1 | 4/2010 | Say et al. |
| 2010/0100160 A1 | 4/2010 | Edman et al. |
| 2010/0106098 A1 | 4/2010 | Atterbury et al. |
| 2010/0114026 A1 | 5/2010 | Karratt et al. |
| 2010/0114060 A1 | 5/2010 | Ginngen et al. |
| 2010/0116070 A1 | 5/2010 | Farina et al. |
| 2010/0121314 A1 | 5/2010 | Iobbi |
| 2010/0122697 A1 | 5/2010 | Przekwas et al. |
| 2010/0268111 A1 | 10/2010 | Drinan et al. |
| 2011/0224912 A1 | 9/2011 | Bhavaraju et al. |
| 2011/0230732 A1 | 9/2011 | Edman et al. |

FOREIGN PATENT DOCUMENTS

| | | |
|---|---|---|
| JP | 2008-525063 | 7/2008 |
| WO | WO8102982 | 10/1981 |
| WO | WO8607269 | 12/1986 |
| WO | WO9207599 | 5/1992 |
| WO | WO9209324 | 6/1992 |
| WO | WO9211808 | 7/1992 |
| WO | WO9215353 | 9/1992 |
| WO | WO9217231 | 10/1992 |
| WO | WO9306803 | 4/1993 |
| WO | WO9312823 | 7/1993 |
| WO | WO9405359 | 3/1994 |
| WO | WO9408655 | 4/1994 |
| WO | WO9416755 | 8/1994 |
| WO | WO9416756 | 8/1994 |
| WO | WO9416759 | 8/1994 |
| WO | WO9427653 | 12/1994 |
| WO | WO9507723 | 3/1995 |
| WO | WO9507724 | 3/1995 |
| WO | WO9513838 | 5/1995 |
| WO | WO9526769 | 10/1995 |
| WO | WO9610440 | 4/1996 |
| WO | WO9616686 | 6/1996 |
| WO | WO9625186 | 8/1996 |
| WO | WO9625978 | 8/1996 |
| WO | WO9627341 | 9/1996 |
| WO | WO9630078 | 10/1996 |
| WO | WO9707896 | 3/1997 |
| WO | WO9711655 | 4/1997 |
| WO | WO9711742 | 4/1997 |
| WO | WO9711743 | 4/1997 |
| WO | WO9726934 | 7/1997 |
| WO | WO9733640 | 9/1997 |
| WO | WO9733645 | 9/1997 |
| WO | WO9748431 | 12/1997 |
| WO | WO9800188 | 1/1998 |
| WO | WO9801168 | 1/1998 |
| WO | WO9806450 | 2/1998 |
| WO | WO9814235 | 4/1998 |
| WO | WO9832479 | 7/1998 |
| WO | WO9839057 | 9/1998 |
| WO | WO9844984 | 10/1998 |
| WO | WO9850095 | 11/1998 |
| WO | WO9900144 | 1/1999 |
| WO | WO9930760 | 6/1999 |
| WO | WO9965551 | 12/1999 |
| WO | WO0001434 | 1/2000 |
| WO | WO0007652 | 2/2000 |
| WO | WO0018339 | 4/2000 |
| WO | WO0021598 | 4/2000 |
| WO | WO0027278 | 5/2000 |
| WO | WO0032267 | 6/2000 |
| WO | WO0038770 | 7/2000 |
| WO | WO0043059 | 7/2000 |
| WO | WO0047253 | 8/2000 |
| WO | WO0050111 | 8/2000 |
| WO | WO0053247 | 9/2000 |
| WO | WO0059483 | 10/2000 |
| WO | 01/05463 | 1/2001 |
| WO | 0105463 | 1/2001 |
| WO | WO0113973 | 3/2001 |
| WO | WO0124851 | 4/2001 |
| WO | WO0130419 | 5/2001 |
| WO | WO0158236 | 8/2001 |
| WO | WO0168169 | 9/2001 |
| WO | WO0183007 | 11/2001 |
| WO | WO0185027 | 11/2001 |
| WO | WO0187378 | 11/2001 |
| WO | WO0189607 | 11/2001 |
| WO | WO0200280 | 1/2002 |
| WO | WO0202052 | 1/2002 |
| WO | WO0204043 | 1/2002 |
| WO | WO0217988 | 3/2002 |
| WO | WO0217998 | 3/2002 |
| WO | WO0224257 | 3/2002 |
| WO | WO0224268 | 3/2002 |
| WO | WO0234318 | 5/2002 |
| WO | WO0236181 | 5/2002 |
| WO | WO02053223 | 7/2002 |
| WO | WO02072178 | 9/2002 |
| WO | WO02076533 | 10/2002 |
| WO | WO02078535 | 10/2002 |
| WO | WO02081016 | 10/2002 |
| WO | WO02089879 | 11/2002 |
| WO | WO02089884 | 11/2002 |
| WO | WO02096489 | 12/2002 |
| WO | WO03006091 | 1/2003 |
| WO | WO03008014 | 1/2003 |
| WO | WO03020349 | 3/2003 |
| WO | WO03022327 | 3/2003 |
| WO | WO03028797 | 4/2003 |
| WO | WO03035172 | 5/2003 |
| WO | WO03038566 | 5/2003 |
| WO | WO03045302 | 6/2003 |
| WO | WO03059413 | 7/2003 |
| WO | WO03071930 | 9/2003 |
| WO | WO03073977 | 9/2003 |
| WO | WO03086505 | 10/2003 |
| WO | WO03090821 | 11/2003 |
| WO | WO03097120 | 11/2003 |
| WO | WO2004009161 | 1/2004 |
| WO | WO2004011067 | 2/2004 |
| WO | WO2004012801 | 2/2004 |
| WO | WO2004020024 | 3/2004 |
| WO | WO2004021882 | 3/2004 |
| WO | WO2004022128 | 3/2004 |
| WO | WO2004022153 | 3/2004 |
| WO | WO2004022242 | 3/2004 |
| WO | WO2004026380 | 4/2004 |
| WO | WO2004032989 | 4/2004 |

(56) References Cited

FOREIGN PATENT DOCUMENTS

| | | |
|---|---|---|
| WO | WO2004034998 | 4/2004 |
| WO | WO 2004041334 | 5/2004 |
| WO | WO 2004041339 | 5/2004 |
| WO | WO 2004045690 | 6/2004 |
| WO | WO 2004060436 | 7/2004 |
| WO | WO 2004060443 | 7/2004 |
| WO | WO 2004060447 | 7/2004 |
| WO | WO 2004080522 | 9/2004 |
| WO | WO 2004088567 | 10/2004 |
| WO | WO 2005009514 | 2/2005 |
| WO | WO 2005011779 | 2/2005 |
| WO | WO 2005028008 | 3/2005 |
| WO | WO 2005031317 | 4/2005 |
| WO | WO 2005039750 | 5/2005 |
| WO | WO 2005046559 | 5/2005 |
| WO | WO 2005051177 | 6/2005 |
| WO | WO 2005072798 | 8/2005 |
| WO | WO 2005084275 | 9/2005 |
| WO | WO 2005084738 | 9/2005 |
| WO | WO 2005087299 | 9/2005 |
| WO | WO 2005102412 | 11/2005 |
| WO | WO 2005102417 | 11/2005 |
| WO | WO 2005102418 | 11/2005 |
| WO | WO 2005102428 | 11/2005 |
| WO | WO 2005120615 | 12/2005 |
| WO | WO 2005123002 | 12/2005 |
| WO | WO 2006003665 | 1/2006 |
| WO | WO 2006009596 | 1/2006 |
| WO | WO 2006015299 | 2/2006 |
| WO | 2006/029090 | 3/2006 |
| WO | 2006029090 | 3/2006 |
| WO | WO 2006022714 | 3/2006 |
| WO | WO 2006023644 | 3/2006 |
| WO | WO 2006035443 | 4/2006 |
| WO | WO 2006044206 | 4/2006 |
| WO | WO 2006045524 | 5/2006 |
| WO | 2006/069323 | 6/2006 |
| WO | 2006069323 | 6/2006 |
| WO | WO 2006058426 | 6/2006 |
| WO | WO 2006060106 | 6/2006 |
| WO | WO 2006079898 | 8/2006 |
| WO | WO 2006096286 | 9/2006 |
| WO | WO 2006098933 | 9/2006 |
| WO | WO2006098936 | 9/2006 |
| WO | WO2006113408 | 10/2006 |
| WO | 2006/116718 A2 | 11/2006 |
| WO | 2006116718 | 11/2006 |
| WO | WO2006120253 | 11/2006 |
| WO | WO2006124759 | 11/2006 |
| WO | WO2006125577 | 11/2006 |
| WO | WO2006127257 | 11/2006 |
| WO | WO2006127905 | 11/2006 |
| WO | WO2006127953 | 11/2006 |
| WO | WO2006128794 | 12/2006 |
| WO | WO2006130098 | 12/2006 |
| WO | WO2006133101 | 12/2006 |
| WO | WO2007012854 | 2/2007 |
| WO | 2007/028035 | 3/2007 |
| WO | 2007028035 | 3/2007 |
| WO | WO2007031740 | 3/2007 |
| WO | WO2007034237 | 3/2007 |
| WO | WO2007041158 | 4/2007 |
| WO | WO2007041471 | 4/2007 |
| WO | WO2007051563 | 5/2007 |
| WO | WO2007070093 | 6/2007 |
| WO | WO2007070695 | 6/2007 |
| WO | 2007/120884 | 10/2007 |
| WO | 2007120884 | 10/2007 |
| WO | WO2007125699 | 11/2007 |
| WO | WO2007127981 | 11/2007 |
| WO | WO2007131025 | 11/2007 |
| WO | 2008/008281 A2 | 1/2008 |
| WO | WO2008008281 | 1/2008 |
| WO | WO2008016698 | 2/2008 |
| WO | WO2008021252 | 2/2008 |
| WO | WO2008022010 | 2/2008 |
| WO | WO2008029403 | 3/2008 |
| WO | WO2008030837 | 3/2008 |
| WO | WO2008037801 | 4/2008 |
| WO | WO2008038241 | 4/2008 |
| WO | WO2008039091 | 4/2008 |
| WO | WO2008043724 | 4/2008 |
| WO | WO2008052039 | 5/2008 |
| WO | WO2008073806 | 6/2008 |
| WO | WO2008077706 | 7/2008 |
| WO | WO2008078287 | 7/2008 |
| WO | 2008/095183 A2 | 8/2008 |
| WO | 2008095183 | 8/2008 |
| WO | WO2008103620 | 8/2008 |
| WO | WO2008115906 | 9/2008 |
| WO | WO2008117226 | 10/2008 |
| WO | WO2008127743 | 10/2008 |
| WO | WO2008130801 | 10/2008 |
| WO | WO2008134107 | 11/2008 |
| WO | WO2008134545 | 11/2008 |
| WO | WO2008152588 | 12/2008 |
| WO | WO2008154312 | 12/2008 |
| WO | WO2008154504 | 12/2008 |
| WO | WO2009003989 | 1/2009 |
| WO | WO2009008001 | 1/2009 |
| WO | WO2009013501 | 1/2009 |
| WO | WO2009013670 | 1/2009 |
| WO | WO2009023247 | 2/2009 |
| WO | WO2009035759 | 3/2009 |
| WO | WO2009042379 | 4/2009 |
| WO | WO2009049252 | 4/2009 |
| WO | WO2009063421 | 5/2009 |
| WO | WO2009072079 | 6/2009 |
| WO | WO2009076363 | 6/2009 |
| WO | WO2009079589 | 6/2009 |
| WO | WO2009081262 | 7/2009 |
| WO | WO2009091851 | 7/2009 |
| WO | WO2009098648 | 8/2009 |
| WO | WO2009105337 | 8/2009 |
| WO | WO2009126653 | 10/2009 |
| WO | WO2009137661 | 11/2009 |
| WO | WO2009140251 | 11/2009 |
| WO | WO2009145801 | 12/2009 |
| WO | WO2009155335 | 12/2009 |
| WO | WO2010007573 | 1/2010 |
| WO | WO2010007574 | 1/2010 |
| WO | WO2010008424 | 1/2010 |
| WO | WO2010010473 | 1/2010 |
| WO | WO2010021589 | 2/2010 |
| WO | WO2010023591 | 3/2010 |
| WO | WO2010025428 | 3/2010 |
| WO | WO2010025431 | 3/2010 |
| WO | WO2010029054 | 3/2010 |
| WO | WO2010037828 | 4/2010 |
| WO | WO2010042034 | 4/2010 |
| WO | WO2010043054 | 4/2010 |
| WO | WO2010045460 | 4/2010 |
| WO | WO2010051551 | 5/2010 |
| WO | WO2010052275 | 5/2010 |
| WO | WO2010062675 | 6/2010 |

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

Juvenile Diabetes Research Foundation International (JDRF), "Artificial Pancreas Project" (2010); http://www.artificialpancreasproject.com/; 3 pp.

Lifescan, "OneTouch UltraLink™"http://www.lifescan.com/products/meters/ultralink (N.D.) 2 pp.

Medtronic, "CareLink Therapy Management Software for Diabetes" (2010); https://carelink.minimed.com/patient/entry.jsp?bhcp=1; 1 pp.

Medtronic, "Carelink™ USB" (n.d.) http://www.medtronicdiabetes.com/pdf/carelink_usb_factsheet.pdf 2pp.

Medtronic "The New MiniMed Paradigm® REAL-Time Revel™ System" http://www.medtronicdiabetes.com/products/index.html; 2 pp.

(56) References Cited

OTHER PUBLICATIONS

Medtronic, "Mini Med Paradigm® Revel™ Insulin Pump" (n.d.) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Park, "Medtronic to Buy MiniMed for $3.7 Billion" (2001) HomeCare; http://homecaremag.com/mag/ medical_medtronic_buy_minimed/; 2 pp.

Prutchi et al., "Design and Development of Medical Electronic Instrumentation: A Practical Perspective of the Design, Construction, and Test of Medical Devices" Wiley-Interscience (2005) pp. 12-14.

* cited by examiner

FLUID TRANSFER PORT INFORMATION SYSTEM

CROSS-REFERENCE TO RELATED APPLICATIONS

Pursuant to 35 U.S.C. §119 (e), this application claims priority to the filing date of: U.S. Provisional Patent Application Ser. No. 60/982,661 filed Oct. 25, 2007; the disclosure of which applications is herein incorporated by reference.

INTRODUCTION

The parenteral administration (i.e., administration in a manner other than through the digestive tract, such as by intravenous or intramuscular injection or inhalation) of beneficial agents and fluids is an established clinical practice. Parenteral administration of beneficial agents are effective remedies for many patients when administered properly, e.g., according to instructions. However, studies have shown that, on average, about 10% of patients receive an incorrect injectable medication. For example, a significant percentage of serious errors are associated with the administration of intravenous (IV) medication.

In the clinical setting, misconnections of tubing used to link patients to medical devices have the potential to result in serious injury or death. Medical devices used in hospitals must have the ability to connect to related tubing and accessories. Connection is generally achieved through the standard "luer" connector. However, because the luer connector is a standard size and is used on such a broad range of medical devices and products with totally different functions, the risk for tubing misconnections is great.

A patient, for example, may be connected to several devices used to administer fluids through a vein; deliver feedings via a tube to the stomach; monitor blood pressure; and administer oxygen via mask or cannula. This collection of devices, all of which may include luer connectors, poses a risk of tubing misconnection especially in a busy clinical environment where stress, fatigue and distractions are common.

Misconnections, which have been made between numerous types of medical devices in diverse clinical settings, include but are not limited to the following: enteral feeding tubes mistakenly connected to IV lines; IV tubing connected to the tracheal-cuff pilot balloon port; noninvasive blood pressure (BP) cuffs connected to IV lines; and drugs intended for IV administration given intrathecally.

SUMMARY

Aspects of the invention include systems and methods for associating a specific one of multiple distinct fluid transfer ports in a patient with a given fluid transfer even of a fluid from a parenteral fluid delivery device to that patient. Aspects of the methods include establishing a fluid connection between the parenteral fluid delivery device and the patient via one of the two or more distinct fluid transfer ports. Next, a fluid transfer signal is transmitted between the parenteral fluid delivery device and a patient associated identifier using the patient's body as a signal conduction medium, e.g., from the fluid delivery device to the patient associated identifier or from the patient associated identifier to the fluid delivery device. A parameter of the fluid transfer signal, such as the strength of the fluid transfer signal, is then employed to a specific one of the two or more distinct fluid transfer ports of the patient with the given fluid transfer even. The association may include identification of the specific fluid transfer port that has been, is being or will be employed for the fluid delivery of fluid from the parenteral fluid delivery device to the patient. Where desired, the methods may include production of an error signal upon identification of an error concerning a specific fluid transfer port and a given fluid transfer event.

DETAILED DESCRIPTION

Methods are provided for associating a specific one of two or more distinct fluid transfer ports of a patient with a given fluid transfer event of fluid from a parenteral fluid delivery device. Aspects of the methods include establishing a fluid transfer connection between the parenteral fluid delivery device and the patient via one of the two or more distinct fluid transfer ports and transmitting a fluid transfer signal between the parenteral fluid delivery device and a patient associated identifier using the patient's body as a signal conduction medium. Association may result in identification of the fluid transfer port that will be, is being or has been employed for the given fluid transfer event. Also provided are systems for practicing methods of the invention.

Systems of the invention may include a parenteral fluid delivery device and one or more patient associated identifiers. The parenteral fluid delivery device and the one or more patient associated identifiers are configured so that a fluid transfer signal can be transmitted between the two components using the body of the patient as a communication medium. To employ the body as a conduction medium for the fluid transfer signal, a fluid communication between the fluid delivery device and the patient is first established. As the body of the patient is used as a communication medium, the signal that is transferred between the parenteral fluid delivery device and the patient travels through the body, (e.g., in a direction from the patient associated identifier to the delivery device and/or from the delivery device to the patient associated identifier), and requires the body as the conduction medium. The fluid transfer signal may be conductively transmitted between the fluid delivery device and the patient associated identifier(s) using the patient as a conductive medium.

As the body is required as a conduction medium and requires the establishment of fluid transfer connection between the fluid delivery device and the patient, receipt of the signal (either at the patient associated identifier, the parenteral fluid delivery device or another component of the system, e.g., as reviewed in greater detail below) provides accurate knowledge about a fluid transfer event and a particular fluid transfer port associated with the fluid transfer event, e.g., that will be, is being or has been employed for the fluid transfer event. This accurate knowledge can then be further employed in a variety of different ways, depending on the application, where such applications include prospective, real-time and historic applications. Examples of prospective applications are those applications in which the fluid transfer signal is employed to determine beforehand which of two or more fluid transfer ports associated with a patient is going to be employed for a contemplated (i.e., future) fluid delivery event between the fluid delivery device and the patient. Such applications may further include a determination of whether the particular fluid transfer port is the correct fluid transfer port for the contemplated fluid delivery event. Examples of historic or retrospective applications of the methods and systems of the invention include applications where the fluid transfer signal is employed to obtain an accurate history of a fluid(s) that have been delivered to a patient via a parenteral fluid deliver device, and specifically which of two or more fluid transfer ports have been employed for delivery of the fluid.

As reviewed above, the components of the systems of the invention include a fluid delivery device, one or more patient associated identifiers and two or more fluid transfer ports. The various components are configured such that, during use, a fluid transfer signal is transmitted between them and a parameter of the signal, such as a measure of signal strength, is then employed to identify a particular fluid transfer port via which a fluid delivery event is contemplated or will occur.

In further describing embodiments of the invention, aspects of the systems are further reviewed in greater detail, followed by more detailed discussion of how the systems are employed in methods of fluid transfer port identification.

Systems

Systems of the invention may include a fluid delivery device, one or more patient associated identifiers, and two or more fluid transfer ports, where the systems may further include additional components, e.g., additional communication components, etc.

Parenteral Fluid Delivery Device

The parenteral fluid delivery device of systems of the invention is a device that delivers a quantity of a fluid (e.g., liquid) to a patient by a route other than the digestive tract, e.g., via intravenous delivery, etc. Of particular interest are fluid delivery devices that are configured to interact with a patient associated fluid transfer port via connection element, e.g., by a luer lock fitting. In certain embodiments, the delivery device includes a fluid transfer signal generator, e.g., in the form of an integrated circuit device or other suitable structure, that generates and transmits a signal to a receiver, e.g., which may be part of a patient associated identifier, upon transfer of fluid to the patient. In certain situations, the parenteral fluid delivery device is one that provides for one way transfer of fluid from the device to the patient. For parenteral delivery of a liquid, the delivery device may vary. One type of device of interest is an intravenous administration device, which may include a liquid storage element, e.g., a fluid containment or IV bag, a fluid metering unit or pump, a drip bag, etc. The liquid delivered to the patient may vary greatly in composition, and may include one or more distinct beneficial agents in a liquid pharmaceutically acceptable vehicle, e.g., one or more pharmaceutical agents, or may be a beneficial agent in its own right, e.g., such as where the liquid is a plasma volume expander. Also of interest are delivery devices that provide for transfer of fluid both to and from the patient. Such devices include those where the fluid, e.g., blood, dialysate, etc., is transferred from a patient to an external device and then transferred back from the device to the patient, typically after some type of processing in the device. An example of a parenteral fluid delivery device that finds use in these situations is a dialysis machine, where such devices may be parenteral dialysis devices or hemodialysis devices, etc.

A given fluid delivery device may include a single component or two or more disparate components, e.g., syringes and vials, fluid containment bags and IV pumps, etc.) which are operatively connected to one another during use and collectively have the ability to transfer a fluid transfer signal between the device and a patient associated identifier, as reviewed above. As such, the various components of the systems may further include communication elements, e.g., broadcasters and/or receivers, as may be required or desired for a given embodiment of the system. Such components may further include power sources, as may be desired, where any convenient power source may be present, including those mentioned in connection with the patient associated identifier, below.

Embodiments of the fluid delivery devices may include what are viewed as pharma-informatics enabled components, such as pharma-informatics enabled fluid containers. By pharma-informatics enabled fluid container is meant a fluid container which includes an identifier that provides identifying information about the fluid in the container. The container may vary, where the container may be a, bag, vial, etc., which includes a volume of fluid that is to be transferred to a patient. The nature of the identifying information may vary greatly from the simple, e.g., the name of the fluid, the name of the pharmaceutical agent present therein, to the more complex, e.g., the dosage present in the container, the history of the fluid in the container, the quality of the fluid in the container (e.g., whether it is compromised or spoiled), etc. The nature of the identifier may also vary, e.g., from being a passive interrogatable element, such as a barcode or other machine readable identifier, to a more active component, such as a component that can broadcast information and may include a power source. Sensors, as described below, may also be associated with the medical containers.

Where a given system includes two or more different fluid containers, the system may be configured as a multiplex system. Multiplex systems of interest are configured to sufficiently reduce or eliminate cross-talk and confusion between various broadcast signals of multiple components of the multiplex system such that a given fluid transfer signal about a given fluid and a patient may be properly matched up or associated with each other. For example, a signal generated about a first IV bag may be distinguishable from a signal generated about a second bag, where distinguishable signals may be provided in a number of different ways, e.g., by using an appropriate time based communication protocol, by having signals of different frequencies, etc. Of interest are the signal protocols described in PCT/US2006/016370 filed on Apr. 28, 2006, the disclosure of which is herein incorporated by reference. In certain embodiments where multiple different fluid containers are present in a given fluid delivery system, the different fluids may be color coded to provide an additional distinguishing feature, where this color coding may be detected and transmitted to the patient associated identifier (e.g., as part of a fluid transfer signal) for further confirmation that the right medicine, e.g., composition, dosage, quality, etc., is being delivered to the right patient.

Parenteral fluid delivery devices of interest, including examples of circuitry that may be used therein for the broadcaster and/or receiver elements thereof, are further described in PCT application serial no. PCT/US2007/015547 titled "Smart Parenteral Administration System" and filed on Jul. 6, 2007; the disclosure of which is herein incorporated by reference.

Patient Associated Identifier

As summarized above, a component of the systems of the invention is one or more patient associated identifiers. The patient associate identifier is a device that is configured to be associated with the patient, e.g., either topically or by implantation, and includes a communications element that performs at least one of broadcasting and receiving functions. The patient associated identifier is one that at least provides for broadcast and/or receipt of a fluid transfer signal, where the signal may comprise a variety of different types of information, such as identifying information about the patient. The identifier can be configured in a variety of different ways, including formats that are configured to simply broadcast a signal to more complex formats where the identifier receives information about a fluid transfer event (e.g., where the patient associated identifier includes a receiver element) and internally processes that information to evaluate the fluid transfer event in some manner. For example, the identifier may have a memory containing pre-existing knowledge of which medications are to be delivered to the patient. The identifier may compare the identifying information in the signal to the information in the memory to confirm that the medication associated with the fluid transfer event is correct. If it is not correct, the patient associate identifier may generate an error signal, e.g., as described in greater detail below. The identifiers may be configured to simply broadcast a signal, which may include identifying information about the patient, to the fluid delivery device. Alternatively, the identifiers may be configured to receive a signal from the fluid delivery device. In these cases, the identifiers are signal receivers that are configured to receive a signal from a parenteral fluid delivery device enabled to transmit a fluid transfer signal.

Where desired, the patient associated identifier may be one that is sized to be stably associated with a living subject in a manner that does not substantially impact movement of said living subject. In these instances, the patient associated identifier has dimensions that, when employed with a subject, such as a human subject, will not cause the subject to experience any difference in its ability to move. As such, the patient associated identifier is dimensioned such that its size does not hinder the ability of the subject to physically move. In certain embodiments, the patient associated identifier has a small size, where in certain embodiments the signal receiver has occupies a volume of space of about 5 cm$^3$ or less, such as about 3 cm$^3$ or less, including about 1 cm$^3$ or less.

The patient associated identifiers of interest include both external and implantable devices. In external embodiments, the patient associated identifier is ex vivo, by which is meant that the receiver is present outside of the body during use. Where the identifiers are external, they may be configured in any convenient manner, where in certain embodiments they are configured to be associated with a desirable skin location. As such, in certain embodiments the external signal receivers are configured to be contacted with a topical skin location of a subject. Configurations of interest include, but are not limited to: patches, wrist bands, belts, etc. For instance, a watch or belt worn externally and equipped with suitable receiving electrodes can be used as signal receivers in accordance with one embodiment of the present invention. By further example, it could be positioned by a harness that is worn outside the body and has one or more electrodes that attach to the skin at different locations. In these external embodiments, a portion of the patient associate identifier, e.g., electrode, contacts the skin in a manner such that a communication line that includes the patient's body, e.g., a conductive communication line, may be established between the identifier and a fluid delivery device during use of the system.

Patient associated identifiers of interest also include implantable components. By implantable is meant that the identifier is designed, i.e., configured, for implantation into a patient, e.g., on a semi-permanent or permanent basis. In these instances, the signal receiver is in vivo during use. By implantable is meant that the patient associated identifiers are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In certain embodiments, the implantable circuits are configured to maintain functionality when implanted at a physiological site for a period ranging from about 1 to about 80 years or longer, such as from about 5 to about 70 years or longer, and including for a period ranging from about 10 to about 50 years or longer.

Where the patient associated identifiers are implantable, the identifiers may have any convenient shape, including but not limited to: capsule-shaped, disc-shaped, etc. The patient associated identifiers may have any convenient power source, which could either be a primary cell or rechargeable battery, or one that is powered by broadcast inductively to a coil, or even a photoelectric or other power source, as may be appropriate for the identifier given its site of association with the patient (e.g., topical or internal) and expected operating conditions. Implantable patient associated identifiers of interest include a rechargeable battery, e.g., one that recharges automatically from a power transmitter, e.g., coils, present in the patient's environment, e.g., associated with the patient's bed. The patient associated identifier may be configured to be placed in a number of different locations, e.g., the abdomen, small of the back, shoulder (e.g., where implantable pulse generators are placed), etc.

In addition to being configured to participate in transmission of a signal between the identifier and a fluid delivery device using the patient's body as a conduction medium, the patient associated identifier may further include one or more distinct physiological parameter sensing abilities. By physiological parameter sensing ability is meant a capability of sensing a physiological parameter or biomarker, such as, but not limited to: heart rate, respiration rate, temperature, pressure, chemical composition of fluid, e.g., analyte detection in blood, fluid state, blood flow rate, accelerometer motion data, IEGM (intra cardiac electrogram) data, etc.

Patient associated identifiers of the invention may be configured to provide a further communication path via which collected data can be extracted by a patient or health care practitioner. For instance, an implanted collector may include conventional RF circuitry (operating, e.g., in the 405-MHz medical device band) with which a practitioner can communicate, e.g., using a data retrieval device, such as a wand or analogous device. Where the patient associated identifier includes an external component, that component may have output devices for providing, e.g., audio and/or visual feedback; examples include audible alarms, light emitting diodes, display screens, or the like. The external component may also include an interface port via which the component can be connected to a computer for reading out data stored therein. In these instances, the circuitry of the patient associated identifier may be configured to receive signals from devices inside of the subject, e.g., from an identifier of a pharma-informatics enabled pharmaceutical composition, and then relay this information to an external processing device, e.g., a PDA, smartphone, etc.

Of interest in certain situations are parenteral fluid delivery devices that are configured to transmit the fluid transfer signal only when fluid is delivered from the device to the patient and in a manner such that transmission of the signal can only occur when the device actually contacts patient and fluid is transferred to the patient. As such, the system is distinguished from other systems which provide for generation of a signal when a package is opened, or other proxy-type signals for actual administration of the fluid. Instead, the system of the invention provides a signal which provides information that delivery of the fluid to the patient actually occurred, e.g., by only transmitting the signal when the device touches the patient and fluid enters the patient from the device. While the fluid transfer signal may be transmitted between the parenteral fluid delivery device and the patient associated identifier using any convenient protocol, in certain embodiments protocols that ensure transmission only occurs upon contact of the device with the patient are employed. One such protocol of interest is conductive transmission, e.g., where the body is employed as a conductive medium between the fluid delivery device and the patient associated identifier to provide for transmission of the signal.

Patient associated identifiers of interest, including examples of circuitry for the broadcaster and/or receiver elements thereof, include, but are not limited to, those described in: PCT/US2006/16370 titled "Pharma-Informatics System" and filed on Apr. 28, 2006; PCT/US2007/015547 titled "Smart Parenteral Administration System" and filed on Jul. 6, 2007; and PCT/US2008/52845 titled "Ingestible Event Marker Systems" and filed on Feb. 1, 2008; the disclosures of which are herein incorporated by reference.

Fluid Transfer Ports

Fluid transfer ports that are part of systems of the invention may vary widely. In certain embodiments, the ports are partially implanted, while in other embodiments the ports are fully implanted, as is known in the art. The ports may vary from simple to complex, and where desired may include a connector element, e.g., luer lock, for mating with a fluid conveyer, e.g., IV catheter, IV line, etc., of the fluid delivery device. A patient may include two or more fluid transfer ports, such as three or more, four or more, five or more, etc., where the distinct fluid transfer ports are positioned as different locations of the body, e.g., in the neck/collarbone region, on the arms, on the legs, etc.

Additional System Components

As detailed below, certain embodiments are characterized in that the patient associated identifier and/or the fluid delivery device further transmits a signal to and/or receives a signal from an additional external component. The external component is, in certain embodiments, an external processing component, such that it is designed to accept data, perform prescribed mathematical and/or logical operations, and output the results of these operations. Examples of external components of interest include, but are not limited to: a healthcare provider network (e.g., a hospital information system (HIS); a home healthcare information system, etc). Accordingly, systems of the invention may further include an external processor component, such as a hospital information system (HIS) or analogous system that includes various aspects of a patient specific data, such as a prescriptions, treatment regimens, health history, dosage guidelines, etc. This data may include information obtained from an electronic medication storage unit, e.g., a Pyxis system, etc.

The systems may further include various sensors. Physiological sensors may be associated with the patient, and may or may not be part of the patient associated identifier. Physiological sensors of interest include, but are not limited to: heart rate sensors, breathing sensors, temperature sensors, etc., as described more fully above in connection with the patient associated identifier.

Sensors may also be associated with various components of the fluid delivery system. Sensors may be associated with fluid containers, e.g., to detect a color-coded liquid therein, to detect clarity of a fluid, to detect the presence of one or more analytes in the fluid, etc. Sensors may also be present in tubing components of the system, e.g., to detect proxies of bacterial infection, such as turbidity, etc.

Fluid Transfer Signal

As reviewed above, systems of the invention are configured to transfer a fluid transfer signal between the patient associated identifier and the fluid delivery device, where the signal is transferred between these two components using the patient's body as a signal conduction medium. The physical nature of the signal may vary, e.g., where physical types of signals of interest include electric, magnetic, optical, thermal, acoustic, etc. Because the fluid transfer signal is transferred between the two components using the patient's body as a conduction medium, fluid communication is established between the parenteral fluid delivery device and the patient prior to transmission of the fluid transfer signal.

The content of the fluid transfer signal may vary depending on the particular application in which the methods and systems are employed, where the content may range from simple to complex, depending on the particular type of application, e.g., prospective, real-time or historical, the direction, e.g., to and/or from the patient associated identifier, etc. A given fluid transfer signal provides prospective information about a fluid transfer event if the fluid transfer event is a future fluid transfer event, i.e., the fluid transfer event has not yet occurred. A given fluid transfer signal provides real-time information about a fluid transfer event if the fluid transfer event is a currently occurring fluid transfer event, i.e., the fluid transfer currently happening. A given fluid transfer signal provides retrospective information about a fluid transfer event if the fluid transfer event is a past fluid transfer event, i.e., the fluid transfer event has already occurred.

In certain embodiments, the content of the fluid transfer signal is that a fluid connection has been established between the fluid delivery device (including disparate components thereof) and the patient. In certain embodiments, the content of the fluid transfer signal is that of a previously established fluid connection between the fluid delivery device (including disparate components thereof) and the patient has been interrupted. In addition to an indication that a fluid connection has been established, the fluid transfer signal may include additional content, e.g., where additional content of interest includes, but is not limited to: patient specific content, fluid specific content, delivery device specific content, etc.

Patient specific content of interest includes, but is not limited to: identity of patient (e.g., name, unique identifier), general information about the patient, e.g., gender, age, race, etc., health history of patient; health status of patient, including one or more sensed physiological parameters, which may or may not be combined into a health indicative marker, e.g., a wellness marker or index, and the like.

Fluid specific content of interest includes, but is not limited to: identity of the fluid, the contents of the fluid, the identity of one or more pharmacological agents in the fluid, the concentrations of such agents in the fluid, the history of the fluid, e.g., where manufactured, how stored, the quality of the fluid, e.g., whether compromised or not, etc. Also of interest is fluid container specific content, which content includes, but is not limited to: the source/history of the container, the identity of the container, e.g., general (e.g., type such as bag) or specific (e.g., serial no.), etc.

The fluid transfer signal may include information that an actual fluid transfer event has occurred, e.g., a transfer between a parenteral fluid delivery device and a patient. In such embodiments, the fluid transfer signal provides information about whether fluid has been transferred between the parenteral delivery device and the patient. The fluid transfer signal is one that provides for actual knowledge that fluid has been parenterally transferred from the device to the patient.

Accordingly, a given fluid transfer signal may include qualitative or quantitative information. Qualitative information is information that is not tied to specific numerical values or units, and includes but is not limited to: identifying information, quality control information about a fluid (e.g., age, storage conditions, etc.), information about a patient, e.g., how patient is responding, etc., whether something is or is not present, etc. Quantitative information is information that includes numerical values or units, and includes but is not limited to dosage information, etc.

Communication Between System Components

As reviewed above, communication of the fluid transfer signal between the patient associated identifier and the fluid delivery device employs the patient's body as a conductive medium. One or more additional and separate communication lines may be established between various components of the system, such as between the patient associated identifier and an external component, such as a hospital information system, between components of a fluid delivery device, such as an infusion pump and a fluid container, between the fluid delivery device and the hospital information system, etc. These additional communication lines may be wired or wireless communication lines, as desired, employing traditional physical connections, such as wires, optical fibers, etc., or wireless communication protocols, e.g., RFID, etc. These additional communication lines may be employed to transfer information and/or power between the different device components. For example, disparate components of a fluid deliver system may include communications components that are powered via wireless transmission of power from one element to another. These additional communication lines are, in certain embodiments, non-conductive communication lines.

Fluid Transfer Port Identification

As summarized above, the systems as described above are employed in a manner that allows for association of a given fluid transfer event with a specific fluid transfer port. The association may include identification of the specific fluid transfer port that has been, is being or will be employed for a fluid transfer event from a possibility of two or more distinct fluid transfer ports that are associated with a given patient. Accordingly, for those patients that include two or more distinct fluid transfer ports, such as three or more, four or more, etc., the methods and systems of the invention provide for identification of the particular fluid transfer port that has been, is being or will be employed for a given fluid transfer event.

In practicing methods of invention, a parameter of the fluid transfer signal is employed to identify the fluid transfer port that has been, is being or will be used for a given fluid transfer event. The parameter of the fluid transfer signal that is employed is, in certain instances, a non-informational parameter, such as a parameter that does not provide specific information about the patient, nature of the fluid delivery device, nature of the delivered fluid, etc. Instead, the parameter that is employed is a parameter that is independent of any specific content of the signal.

Signal parameters of interest include those parameters that change as a function of distance traveled by the signal between the origin of the signal, e.g., the fluid delivery device or the patient associated identifier, and the destination and/or receiver of the signal, e.g., the patient associated identifier or the fluid delivery device. The parameter may change as a function of distance in either a linear or non-linear manner, depending on the particular nature of the parameter.

One type of parameter that may be employed is a measure of strength of the fluid transfer signal. The fluid transfer signal may consist of a binary signal pattern encoding the information of interest communicated using amplitude modulation, phase key shifting, frequency modulation, or wide-band communication techniques. The parameter that may be employed is the amplitude of the signal, such that the amplitude of the signal at the receiver is employed in determining which of two or more distinct fluid transfer ports will be or has been employed for a given fluid transfer event. In certain embodiments, of interest is an evaluation, e.g., measurement, quantification or other appropriate analysis that provides for comparison to a suitable control, of amplitude of a decoded signal, the envelope strength of a demodulated signal, or statistics related to the time-series or frequency domain characterization of the transmitted signal (i.e., power at specified transmission frequency, standard deviation of time-series transmission packet). Characteristics of the decoded transmission packet, such as signal-to-noise, relative phase, or time-of-detection may also be employed.

In practicing the methods, the parameter of the fluid transfer signal as detected at the receiver component of the system being employed, e.g., the patient associated identifier or the fluid delivery device, is evaluated to determine the identity of the particular fluid transfer port with which the fluid delivery device has established a fluid connection. Evaluation of the signal parameter may include a comparison of the signal parameter to a suitable reference or control value, e.g., an predetermined expected signal parameter value associated with a given fluid transfer port, a comparison to the parameter of the original signal at the fluid transfer port, etc. For example, a patient may have two separate IV ports for use with an IV bag delivery system, where one is located on the left arm and one is located on the right arm. The patient may also have a patient associated identifier located on the right wrist, which acts as a receiver for the fluid transfer signal generated by the IV bag delivery system upon establishment of fluid contact with the patient via one of the two IV ports. The receiver is configured to measure the amplitude of the decoded fluid transfer signal. The signal-to-noise ratio of the signal broadcast by the intelligent IV bag when used to deliver fluid via the IV port on the on the same arm as the patient associated identifier will have a larger amplitude at the patient associated identifier than the signal-to-noise ratio of the signal broadcast by the bag when used to delivery fluid via the IV port on the opposite arm of the receiver. By comparing this measure signal strength at the patient associated identifier on the right wrist to either the signal strength originally broadcast from the fluid delivery device or a predetermined value associated with each of the IV ports, the particular IV port via which fluid communication was established between the fluid delivery device and the patient is identified.

Where the patient has two or more patient associated identifiers associated with different physical locations, e.g., present on each wrist and/or at a torso location, such as the chest, abdomen, etc., one can evaluate the parameter of the signal received at each of the distinct patient associated identifiers and employ derivative and/or triangulation methods to identify the port with which fluid communication was established.

The receiver/evaluation functions performed in practicing the methods may be located at the patient associated identifier or the fluid deliver device, as desired. For example, the signal whose parameter is evaluated in practicing the methods may be one broadcast by the fluid delivery device and received at the patient identifier. Alternatively, the signal whose parameter is evaluated may be one that is broadcast by the patient associated identifier and received at the fluid delivery device. In the latter embodiment, the signal may be one that is continually broadcast, such that it will be broadcast and detected when fluid communication is established by the fluid delivery device via a fluid transfer port. In the former case, the signal may be one that is only broadcast by the fluid delivery device upon establishment of fluid communication.

Where desired, the methods include generating an error signal when the identified fluid transfer port is an incorrect fluid transfer port. For example, the system may be configured to have knowledge regarding which IV ports are to be employed for a given fluid delivery device. When the wrong IV port is employed by a fluid delivery device, the system is configured in these embodiments to produce an error signal. The nature of the error signal may vary, may cause an alarm, e.g., visual and/or sound, to be produced; a message to be sent to a health care manager, e.g., via a hospital information system, etc. Such embodiments are desirable where intervention because of the error is desired, e.g., to counteract any problems caused by the error. In such applications, a processor is conveniently employed to match a port and fluid transfer event specific information, e.g., to determine whether or not to allow the fluid transfer event to occur, to produce an error signal, etc. The location of this processor may vary within the components of the system, as desired. As such, in certain embodiments, the processor may be located in the patient associated identifier. In certain other embodiments, the processor may be located in the fluid delivery device. In yet other embodiments, the processor may be located in the hospital information system.

Where desired, the system may be configured to produce a fluid administration log comprising information about fluid delivery via the two or more distinct fluid transfer ports. The log (i.e., history) that is produced may vary in format, including a recorded file on a suitable computer readable medium which can be output to a user via a user interface of a monitor, a paper printout, etc.

Systems of the invention may be configured to associate a signal fluid transfer port at a time with a given fluid transfer event, or the systems may be configured to associate two or more fluid transfer ports with two or more simultaneous fluid transfer events. For example, the systems may be configured to evaluate fluid transfer events that are simultaneously occurring at each of two or more distinct fluid transfer ports, e.g., where each distinct fluid transfer event has a unique fluid transfer signal that can be distinguished by the receiver component, e.g., present in the patient associate identifier(s).

Applications

The methods of the invention find use in a variety of different applications, including those where one wishes to identify which port of a plurality of two or more distinct fluid transfer ports will be, is being or has been employed for a given fluid transfer event. Certain applications of the systems are prospective applications, in that the system is employed prospectively to evaluate a fluid transfer event (e.g., delivery of a fluid dosage to a patient), where the fluid transfer event has yet to actually occur. Specifically, the prospective applications enable identification of which fluid transfer port will be employed for a fluid transfer event before the event occurs. Such applications include situations where the system is employed as a check to ensure that a given dosage of a fluid is going to be administered to the patient via the correct fluid transfer port. If a proper match is detected between the fluid transfer port and the fluid transfer event of interest, the system can be configured to automatically enable the fluid transfer event to occur, e.g., by activating the fluid delivery device, such as the pump. Alternatively, where a proper match between a fluid transfer port and a given fluid transfer event is not detected, the system can be configured to disable the fluid transfer event, e.g., by inactivating the fluid delivery device, etc.

Where desired, the systems of the invention are configured to provide an error signal upon detection of an error in a parenteral administration event. As such, the systems may be configured to generate an error signal when the wrong port is identified for a given fluid transfer event. The signal may also vary greatly, including an audible alarm, an alarm signal sent to a physician, etc. Such embodiments include methods where the system is monitored for the occurrence of the error signal.

Applications of interest also include real-time applications, where the system is employed to evaluate a fluid transfer event (e.g., which port is employed for delivery of a fluid dosage to a patient), while the fluid transfer event is actually occurring, i.e., is in progress. For example, the system can be used to monitor the patient for an adverse reaction during delivery of the fluid, e.g., by monitoring physiological parameters of the patient. If monitored physiological parameters vary from acceptable predetermined ranges, the system can be configured to produce an error signal, e.g., as described above, and or take action, e.g., investigate the specific port to ensure that the specific port is operating correctly. One example of such an application is where, during a given fluid transfer event, the transfer of fluid is compromised in some manner, e.g., interrupted. The system may be configured to generate a signal indicative of such an interruption, which could be manifested as an alarm, etc., causing the particular functionality of the identified port to be investigated. In response to the error signal, the particular fluid transfer port that may be evaluated, fixed as necessary and/or replaced, e.g., in order to avoid further complications.

Also of interest are uses of the systems and methods for historical applications, such that the systems are employed to obtain a true and correct record of fluid transfer events that have actually occurred between a patient and a fluid delivery device, and specifically which ports have been employed for which specific fluid transfer events. Historical applications are any applications that use information which includes knowledge that a fluid transfer event has actually occurred and which fluid transfer port was employed. True and accurate records of fluid transfer events find use in providing health care practitioners or other individuals of accurate treatment records for a given patient. As such, historical applications include employing the fluid transfer event data in further treatment of an individual, e.g., developing future treatment regimens and/or modifying existent treatment regimens. Additional historical applications of interest include employing the fluid transfer event data for invoicing purposes, e.g., so that patients are accurately billed for medications and/or services that they actually receive, etc. (for example, where compensation is tied to which port is employed, accurate records of port employment are obtained for such invoicing purposes).

Specific Illustrative Embodiments of the Methods and Systems

Aspects of the invention having been described in general terms above, additional details in the context of specific embodiments are now provided. One embodiment of an IV fluid delivery system according to the invention is shown in FIG. 1.

Figure 1:
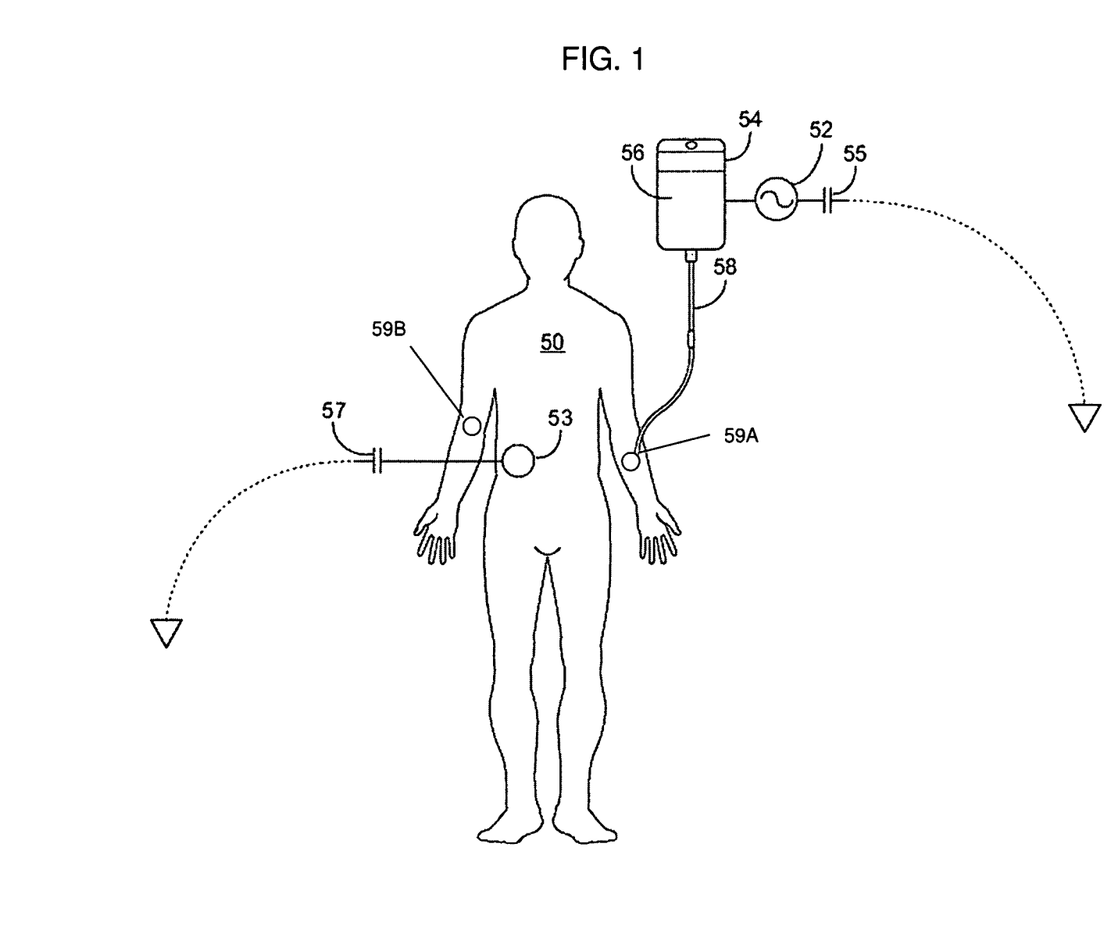
FIG. 1 illustrates an IV bag delivery system according to a first embodiment of the invention.

As shown in FIG. 1, a transmitter 52 is attached to the IV bag 56 or the IV set, which is anything connected to the IV bag, and a receiver 53, which is also referred to as a patient associated identifier, is implanted in the patient. When the IV bag is not connected to the patient, the receiver 53 cannot detect the transmitter 52 transmitting from the IV bag 54. But when the IV bag is infusing fluid, or there is a fluid connection between the IV bag 54 and the receiver 53 via the patient 50 acting as a conducting bridge, or at least attached to the arm in anticipation of delivery of fluid from the IV bag to the patient, then a signal is transmitted by the IV bag 54 and received by the receiver 53.

During operation, the transmitter capacitively couples a signal to the fluid. That signal transmits through the fluid and to the patient, through the patient's body, and to the receiver, e.g., one electrode of the receiver (thereby making up one side of the conductive loop). The other side of the conductive loop is that on the other side of the transmitter, which capacitively couples a signal to ground, which is everything surrounding a patient which is not attached to the patient. The ground could be chairs, tables, the floor, etc. The signal goes through the ground and then is capacitively coupled to the other side of the patch receiver, thereby completing the loop. This capacitive coupling on either side to ground is illustrated in the FIG. 1 by capacitors and dashed arrows 55 and 57, respectively.

Referring to 1, starting at transmitter 52, the fluid signal goes through the bag 54, which is the container or IV bag, and is capacitively coupled through the IV bag. Then the signal progresses to the fluid in the IV bag 56 through the IV tube 58, through the patient's arm, or a vein somewhere in the body, e.g., arm, leg or elsewhere in the body. The signal continues to go through the body to the receiver 53. On the other side of the receiver, a capacitive coupling 57 between the receiver housing and the ground is provided to give a differential signal. The loop is completed through the ground and back up through the capacitive coupling 55 from the ground to the broadcaster, which is attached to the IV bag.

The fluid transfer signal may be a high frequency signal, e.g., between 1 and 10 MHz, and may be higher, e.g., 100 MHz or more, e.g., 1 GHz or more. The frequency is in a range such that the receiver only picks up the signal when the IV bag is connected to the body, and not just by the electromagnetic waves that are emitted by the broadcaster. In certain embodiments, the frequency is chosen based on the considerations that the higher the frequency, the easier it is to couple it directly to the IV bag, but the more likely it is that the signal will be picked up by the receiver regardless of whether the IV bag is connected to the body.

In certain embodiments, the fluid transfer signal also encodes a number, either through phase shift keying, or through frequency shift keying, or one of any other telecommunication convenient technique.

Also shown in FIG. 1 are fluid transfer ports 59A and 59B. By evaluating a parameter of the fluid transfer signal at receiver 53, identification that port 59A is being employed for the fluid transfer event with bag 56 is made.

Figure 2:
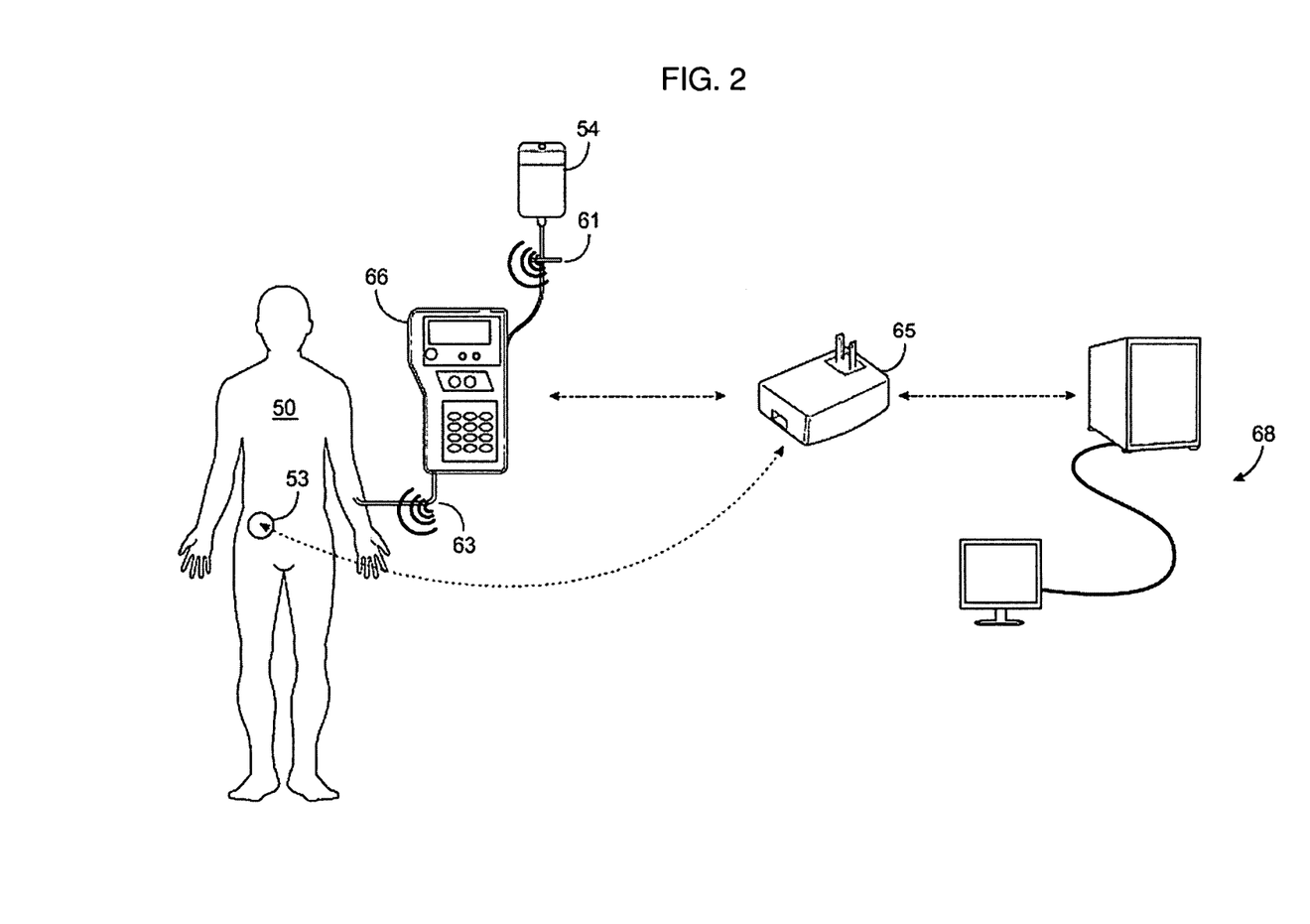
FIG. 2 illustrates an IV bag delivery system according to a second embodiment of the invention.

A variation of this system is where there are two separate links. One of the links goes from an IV bag via a fluid processing unit, e.g., a pump. A second of the links is established between the processing unit and the patient. Such an embodiment is illustrated in FIG. 2. A transconduction link 61 goes from the IV bag 54 into the IV pump 66. A second transconduction link 63 goes from the IV pump 66 to the patient 50, e.g., via one of multiple fluid transfer ports (not shown). If, for example, there are any processing or filtering, or additional chemicals at the IV pump, a different signal may be transmitted to the body which is distinct from the signal transmitted from the IV bags. For example, if there are two different IV bags that are being mixed by the pump, and delivered immediately after being mixed, each of them would be broadcasting identifying information about one of the solutions to the IV pump, and a different signal reflecting that combination being administered to the patient would be broadcast from the pump 66 to the patient associated identifier 53.

Still referring to FIG. 2, the entire system is depicted, where the patient associated identifier 53 broadcasts via an RF link to one or more external devices, e.g., a network of relay stations 65, handheld devices, personal digital assistants, e.g., smart phones, etc. The transmitted data may be data that have been gathered over time, or obtained immediately following reception of delivery data, or even instantaneous data. The data may be further communicated, e.g., via an RF link to a relay station, which then may be further communicated, e.g., through either an RF link or a conductive path link such as a cable or any other type of telecommunication link to an external processing component 68, such as a Health Information System or Service or Server (Hospital Information System (HIS)) within the hospital or care facility. Then this information is processed an output, e.g., recorded to a physical recordable medium, displayed to a user, etc., such as displayed to a nurse or other medical practitioner.

Where desired, the external processor 68 can provide various alerts. For example, an IV bag could have bar codes on it for shipping and receiving purposes, and also before for providing information to be transferred before the contents of the bag are administered to the patient. For example, a given medical fluid container with fluid may be bar coded and entered into the health information system (hospital information system). The prescription for a given patient with respect to that medical fluid container may also be entered into the health information system, and that prescription may be downloaded into the patient's patient associated identifier, e.g., through an RF link. In addition, the same information may be downloaded, for example to the IV pump that is being used to deliver the fluid inside the container to the patient. The IV pump, for example, may only permit delivery after two confirmations occur. In addition, the system may be configured to confirm that the correct IV port will be employed for delivery of the fluid.

In certain embodiments, the port identification information obtained with methods and systems of the invention can also be linked to an internet system. For example, by using a wireless communication protocol, the port identification information can be broadcasted to a hospital bedside monitor. The bedside monitor may then be configured to relay the information to the internet and subsequently to the data base management system. As such, the patient's medical record and IV port usage information is immediately updated and could be verified against the patient's health record so that if the administered medicine was incorrectly administered via the wrong port, an alert to an appropriate individual, e.g., a nursing staff member may be made.

Kits

Also provided are kits for practicing the subject methods. Kits may include one or more receivers of the invention, as described above. In addition, the kits may include one or more parenteral fluid deliver devices, e.g., IV bags, etc.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A method of associating a specific fluid transfer port with a given fluid transfer event of fluid to a patient from a parenteral fluid delivery device, the method comprising:
   transmitting a conductive fluid transfer signal from the parenteral fluid delivery device to a patient associated identifier by capacitively coupling the conductive fluid transfer signal to the fluid infused to the patient from the parenteral fluid delivery device, wherein the patient associated identifier is configured to use a patient's body as a signal conduction medium upon establishment of a fluid transfer connection between the parenteral fluid delivery device and the patient, and wherein the parenteral delivery device is coupled to the patient using a plurality of fluid transfer ports; and
   determining which of the plurality of fluid transfer ports is employed for the given fluid transfer event based on a parameter of the conductive fluid transfer signal; and
   wherein the parameter varies with respect to distance traveled by the fluid transfer signal.

2. The method according to claim 1, wherein the parameter is a measure of signal strength of the fluid transfer signal.

3. A method of associating a specific fluid transfer port with a given fluid transfer event of fluid to a patient from a parenteral fluid delivery device, the method comprising:
   transmitting a conductive fluid transfer signal from the parenteral fluid delivery device to a patient associated identifier by capacitively coupling the conductive fluid transfer signal to the fluid infused to the patient from the parenteral fluid delivery device, wherein the patient associated identifier is configured to use a patient's body as a signal conduction medium upon establishment of a fluid transfer connection between the parenteral fluid delivery device and the patient, and wherein the parenteral delivery device is coupled to the patient using a plurality of fluid transfer ports; and
   determining which of the plurality of fluid transfer ports is employed for the given fluid transfer event based on a parameter of the conductive fluid transfer signal; and
   transmitting an acknowledgement of the conductive fluid transfer signal from the patient associated identifier to the parenteral fluid delivery device.

4. The method according to claim 3, wherein the patient associated identifier and the parenteral fluid delivery device are further configured to communicate non-conductively.

5. The method according to claim 3, further comprising transmitting a signal from at least one of the patient associated identifier or the parenteral fluid delivery device to an external processing system.

6. The method according to claim 5, wherein the external processing system is a hospital information system.

7. The method according to claim 3, further comprising generating an error signal when the associated fluid transfer port is an incorrect fluid transfer port.

8. The method according to claim 3, further comprising producing a fluid administration log comprising information about fluid delivery via the plurality of fluid transfer ports.

9. A system comprising:
   a parenteral fluid delivery device configured to transmit a conductive fluid transfer signal;
   a patient associated identifier configured to be associated with a patient, and wherein the patient associated identifier is configured to use a patient's body as a signal conduction medium upon establishment of a fluid transfer connection between the parenteral fluid delivery device and the patient; and a plurality of fluid transfer ports, wherein each one of the plurality of fluid transfer ports is configured to couple the parenteral fluid delivery device or another fluid delivery device with the patient; and wherein the parenteral fluid delivery device is configured to transmit the conductive fluid transfer signal to the patient associated identifier by capacitively coupling the conductive fluid transfer signal to fluid of the parenteral fluid delivery device infused to the patient; and wherein at least one of the parenteral fluid delivery device and the patient associated identifier is configured to determine which of the plurality of fluid transfer ports is employed for a fluid transfer event associated with the parenteral fluid delivery device based on a parameter of the fluid transfer signal.

10. The system according to claim 9, wherein the patient associated identifier further comprises a transmitter for transmitting a signal acknowledging the conductive fluid transfer signal to the parenteral fluid delivery device, and wherein the parenteral fluid delivery device further comprises a receiver for receiving the signal acknowledging the conductive fluid transfer signal from the patient associated identifier.

11. The system according to claim 9, wherein said system further comprises an external processing system.

12. The system according to claim 11, wherein said external processing system is a hospital information system.

13. The system according to claim 9, wherein the system is configured to produce an error signal when the determined specific fluid transfer port is an incorrect fluid transfer port for the fluid transfer event.

14. The system according to claim 9, wherein the system is configured to produce a fluid administration log comprising information about fluid delivery via the plurality of fluid transfer ports.

15. The system according to claim 9, wherein the patient associated identifier is configured to be associated with the patient by coupling the patient associated identifier to the patient topically or by implantation.

16. The system according to claim 9, wherein the patient associated identifier and the parenteral fluid delivery device are further configured to communicate non-conductively.

17. A system comprising:
a parenteral fluid delivery device configured to transmit a conductive fluid transfer signal;
a patient associated identifier configured to be associated with a patient, and wherein the patient associated identifier is configured to use a patient's body as a signal conduction medium upon establishment of a fluid transfer connection between the parenteral fluid delivery device and the patient; and
a plurality of fluid transfer ports, wherein each one of the plurality of fluid transfer ports is configured to couple the parenteral fluid delivery device or another fluid delivery device with the patient; and
wherein the parenteral fluid delivery device is configured to transmit the conductive fluid transfer signal to the patient associated identifier by capacitively coupling the conductive fluid transfer signal to fluid of the parenteral fluid delivery device infused to the patient; and
an external processing system configured to receive information regarding a parameter of the fluid transfer signal and to determine which of the plurality of fluid transfer ports is employed for a fluid transfer event associated with the parenteral fluid delivery device based on the parameter of the fluid transfer signal.

18. A method of associating a specific fluid transfer port with a given fluid transfer event of fluid to a patient from a parenteral fluid delivery device, the method comprising:
transmitting a conductive fluid transfer signal from the parenteral fluid delivery device to a patient associated identifier by capacitively coupling the conductive fluid transfer signal to the fluid infused to the patient from the parenteral fluid delivery device, wherein the patient associated identifier is configured to use a patient's body as a signal conduction medium upon establishment of a fluid transfer connection between the parenteral fluid delivery device and the patient, and wherein the parenteral delivery device is coupled to the patient using a plurality of fluid transfer ports;
determining which of the plurality of fluid transfer ports is employed for the given fluid transfer event based on a parameter of the conductive fluid transfer signal;
generating an error signal when the associated fluid transfer port is an incorrect fluid transfer port; and
disabling the parenteral fluid delivery device upon receiving the error signal.

* * * * *